US 7,652,011 B2

(12) United States Patent
Bosch et al.

(10) Patent No.: US 7,652,011 B2
(45) Date of Patent: Jan. 26, 2010

(54) 4-[(ARYLMETHYL)AMINOMETHYL] PIPERIDINE DERIVATIVES, THEIR PREPARATION AND THEIR THERAPEUTIC APPLICATION

(75) Inventors: Michael Bosch, Marsillargues (FR); Jean Wagnon, Montpellier (FR)

(73) Assignee: sanofi-aventis, Paris (FR)

( * ) Notice: Subject to any disclaimer, the term of this patent is extended or adjusted under 35 U.S.C. 154(b) by 177 days.

(21) Appl. No.: 11/420,505

(22) Filed: May 26, 2006

(65) Prior Publication Data
US 2007/0037819 A1    Feb. 15, 2007

Related U.S. Application Data

(63) Continuation of application No. PCT/FR2004/03066, filed on Nov. 30, 2004.

(30) Foreign Application Priority Data
Dec. 1, 2003   (FR) ................... 03 14172

(51) Int. Cl.
C07D 401/04 (2006.01)
C07D 295/04 (2006.01)
A61K 31/495 (2006.01)
A61K 31/496 (2006.01)
A61K 31/505 (2006.01)
A61P 25/02 (2006.01)
A61P 25/04 (2006.01)

(52) U.S. Cl. .................. 514/252.11; 514/252.16; 514/269; 544/357; 544/295; 544/238

(58) Field of Classification Search ............ 514/252.02, 514/252.11, 269; 544/238, 295, 357
See application file for complete search history.

(56) References Cited

U.S. PATENT DOCUMENTS
6,689,797 B2   2/2004   Baroni et al.

2005/0176722 A1   8/2005   Bono et al.
2006/0167007 A1   7/2006   Bono et al.

FOREIGN PATENT DOCUMENTS
WO   WO 00/69828   11/2000
WO   WO 00/69829   11/2000

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Allen and Dawbarn, "Clinical relevance of the neurotrophins and their receptors" Clinical Science, vol. 110, pp. 175-191 (2006).*
Vippagunta et. al. (Advanced Drug Delivery Reviews, 2001, 48, pp. 3-26).*

* cited by examiner

Primary Examiner—Brenda L Coleman
Assistant Examiner—Susanna Moore
(74) Attorney, Agent, or Firm—Brian R. Morrill

(57) ABSTRACT

The invention relates to 4-[(arylmethyl)aminomethyl]piperidine derivatives of general formula (I)

(I)

in the form of a base or an addition salt with an acid, and also in the form of a hydrate or solvate, and their preparation process and therapeutic application.

14 Claims, No Drawings

4-[(ARYLMETHYL)AMINOMETHYL] PIPERIDINE DERIVATIVES, THEIR PREPARATION AND THEIR THERAPEUTIC APPLICATION

The present application is a Continuation of International Application No. PCT/FR2004/03066, filed Nov. 30, 2004, which is incorporated by reference herein by its entirety.

FIELD OF THE INVENTION

The present invention relates to substituted 4-[(arylmethyl)aminomethyl]piperidine derivatives, their preparation and their therapeutic application.

The compounds according to the present invention exhibit affinity for the neurotrophin receptor $p75^{NTR}$.

BACKGROUND OF THE INVENTION

Neurotrophins belong to a family of proteins which possess a similar structure and similar functions and include nerve growth factor (NGF), BDNF (Brain Derived Neurotrophic Factor), neurotrophin-3 (NT-3), neurotrophin-4/5 (NT-4/5) and neurotrophin-6 (NT-6). The biological effects of these proteins (survival and differentiation) are exerted through interaction with membrane receptors having tyrosine kinase activity (trk-A, trk-B and trk-C) (H. THOENEN, Science, 1995, 270, 593-598; G. R. LEWIN and Y. A. BARDE, Annu. Rev. Neurosci., 1996, 19, 289-317; M. V. CHAO, J., Neurobiol., 1994, 25, 1373-1385; M. BOTHWELL, Annu. Rev. Neurosci., 1995, 18, 223-253; G. DECHANT and Y. A. BARDE, Curr. Opin. Neurobiol., 1997, 7, 413-418). However, many studies show the preponderant role of the $p75^{NTR}$ receptor in the activity of neurotrophins.

The $p75^{NTR}$ receptor, the receptor for all neurotrophins, is a transmembrane glycoprotein of the tumour necrosis factor (TNF) receptor family (W. J. FRIEDMAN and L. A. GREENE, Exp. Cell. Res., 1999, 253, 131-142; J. MELDOSIS et al., Trends Pharmacol. Sci., 2000, 21, 242-243). A number of biological functions are attributed to the $p75^{NTR}$ receptor: on the one hand, the modulation of the affinity of neurotrophins for trk receptors; on the other hand, in the absence of trk, induction of a signal for cell death by apoptosis which occurs through homodimerization of the receptor and activation of the ceramide pathway.

Apoptosis, or programmed cell death, is a physiological mechanism for elimination of cells in numerous tissues. In particular, apoptosis plays a preponderant role in embryogenesis, morphogenesis and cell renewal. Apoptosis is a genetically controlled phenomenon which only occurs at an advanced and irreversible stage of cell lesion.

Many studies show that apoptosis occurs in several pathologies of the central nervous system such as amyotrophic lateral sclerosis, multiple sclerosis, Alzheimer's, Parkinson's and Huntington's diseases and prion diseases. Furthermore, neuronal death through apoptosis also occurs very early after cerebral and cardiac ischaemia. Cell death is also a preponderant phenomenon in atherosclerosis; indeed, the necrosis zones in primary atherosclerotic lesions in humans are evaluated at 80% (M. L. BOCHATON-PIALAT et al., Am. J. Pathol., 1995, 146, 1-6; H. PERLMAN, Circulation, 1997, 95, 981-987). Apoptosis is also involved in mechanisms leading to cell death following cardiac ischaemia-reperfusion (H. YAOITA et al., Cardiovasc. Res., 2000, 45, 630-641).

Several studies show that the $p75^{NTR}$-dependent pro-apoptotic signal is observed in various cell types including neuronal cells, oligodendrocytes, Schwann cells and also hepatic, cardiac and smooth muscle cells (J. M. FRADE et al., Nature, 1996, 383, 166-168; P. LASACCIA-BONNEFIL et al., Nature, 1996, 383, 716-719; M. SOILU-HANNINEN et al., J. Neurosci., 1999, 19, 4828-4838; N. TRIM et al., Am. J. Pathol., 2000, 156, 1235-1243; S. Y. WANG et al., Am. J. Pathol., 2000, 157, 1247-1258). Moreover, a number of experiments carried out in vivo show an increase in the expression of $p75^{NTR}$ following ischaemia in regions of the brain and of the heart in which massive apoptosis is recorded. These results therefore suggest that $p75^{NTR}$ may play a preponderant role in the mechanisms leading to neuronal death through apoptosis post ischaemia (P. P. ROUX et al., J. Neurosci., 1999, 19, 6887-6896; J. A. PARK et al., J. Neurosci., 2000, 20, 9096-9103).

The $p75^{NTR}$ receptor is described as a cellular target for the prion peptide (V. DELLA-BIANCA et al., J. Biol. Chem., 2001, in press) and for the β-amyloid peptide (S. RABIZADEH et al., Proc. Natl. Acad. Sci. USA, 1994, 91, 10703-10706) and would thus be involved in apoptotic phenomena induced by these compounds. These results support the hypothesis according to which $p75^{NTR}$ would play an important role in neuronal death induced by the infectious prion protein (transmissible spongiform encephalopathy) or by the beta-amyloid protein (Alzheimer's disease).

Recent studies suggest that the $p75^{NTR}$ receptor might also play an important role in axonal regeneration, via its function as co-receptor for the Nogo receptor (WONG et al., Nature Neurosci., 2002, 5, 1302-1308; Kerracher and Winton, Neuron, 2002, 36, 345-348). Indeed, several myelin-associated proteins (myelin-associated glycoprotein, MAG, Nogo-A and oligo-dendrocyte myelin glycoprotein OMgp) inhibit nerve regeneration at the central level during medullary or cranial trauma. These proteins are located in the membrane of the oligodendrocytes directly adjacent to the axon and inhibit meuritic growth by binding with a high affinity to the Nogo receptor located on the axonal membrane. The $p75^{NTR}$ receptor is associated with the Nogo receptor and is involved in the signalling of the inhibitory effects of these myelin proteins in relation to axonal growth. As a result, the $p75^{NTR}$ receptor plays a major role in the regulation of neuronal plasticity and in neuron-glia interactions and represents a therapeutic target of choice for promoting nerve regeneration.

At the peripheral level, recent studies show an increase in the expression of $p75^{NTR}$ and of neurotrophins and a massive apoptosis in atherosclerotic lesions. Furthermore, a pro-angiogenic and vasodilative effect of NGF is also recorded. Finally, a novel form of $p75^{NTR}$ which is truncated in the extracellular part has been identified as well as its major role in established vasculogenesis (D. VON SHACK et al., Nature Neuroscience, 2001, 4, 977-978). All these recent data suggest that $p75^{NTR}$ in its whole or truncated form could also play a preponderant role in vascular pathologies.

A number of compounds are known to interact with the trkA/NGF/$p75^{NTR}$ system or to possess an NGF-type activity. Thus, patent application WO 00/59893 describes substituted pyrimidine derivatives which demonstrate an NGF-type activity and/or which increase the activity of NGF on PC12 cells. Patent applications WO 00/69828 and WO 00/69829 describe polycyclic compounds which inhibit the binding of NGF to the $p75^{NTR}$ receptor in cells which do not express the trkA receptor. Application WO 94/11373 describes pyridazinoquinazolone derivatives which bind to the neurotrophin receptor $p75^{NTR}$. Application WO 94/22866 describes pyrazoloquinazolone derivatives which specifically bind to NGF so as to avoid its attachment to the $p75^{NTR}$ receptor but allowing it to interact with the trk receptor. Application WO 01/49684 describes substituted tetrahydropyridine derivatives which possess activity vis-à-vis the modulation of TNF-alpha.

New 4-[(arylmethyl)aminomethyl]piperidine derivatives have now been found which exhibit affinity for the receptor p75$^{NTR}$.

SUMMARY OF THE INVENTION

The present invention provides compounds of the formula (I):

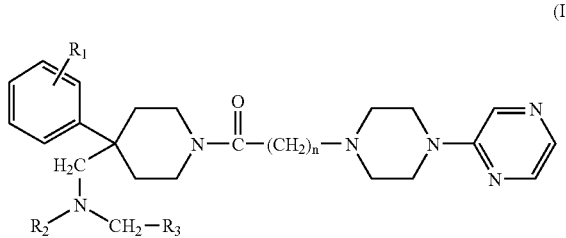

in which:

n is 1 or 2;

$R_1$ represents a trifluoromethyl radical;

$R_2$ represents a hydrogen atom or a ($C_1$-$C_3$)alkyl;

$R_3$ represents an aromatic group selected from:

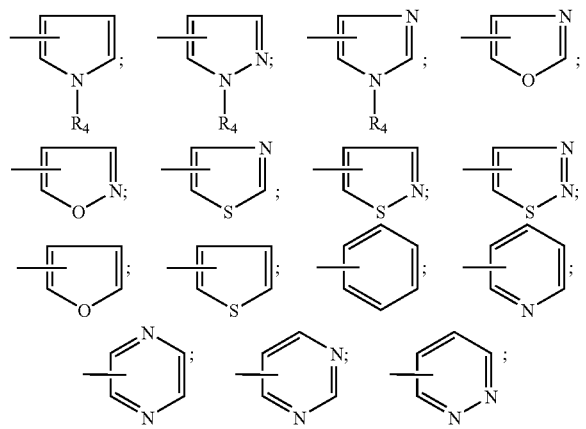

the said aromatic groups being unsubstituted or being mono- or disubstituted by a substituent selected independently from a halogen atom; a ($C_1$-$C_3$)alkyl or a ($C_1$-$C_3$)alkoxy;

$R_4$ represents a hydrogen atom or a ($C_1$-$C_3$)alkyl.

DETAILED DESCRIPTION OF THE INVENTION

The compounds of formula (I) may exist in the form of bases or addition salts with acids. Such addition salts form part of the invention.

These salts are advantageously prepared with pharmaceutically acceptable acids, although the salts of other acids useful for the purification or isolation of compounds of formula (I) also form part of the invention.

The compounds of formula (I) may also exist in the form of hydrates or solvates, specifically in the form of associations or combinations with one or more molecules of water or with a solvent. Such hydrates and solvates also form part of the invention.

A halogen atom is an atom of bromine, chlorine, fluorine or iodine.

($C_1$-$C_3$)Alkyl is a linear or branched alkyl radical of one to three carbon atoms such as the methyl, ethyl, propyl or isopropyl radical.

($C_1$-$C_3$) Alkoxy is a linear or branched alkoxy radical of one to three carbon atoms, such as the methoxy, ethoxy, propoxy or isopropoxy radical.

Among the compounds of formula (I) provided by the invention mention may be made of the preferred compounds which are defined as follows:

n is 1;

and/or $R_1$ is in position 3 of the phenyl and represents a trifluoromethyl radical;

and/or $R_2$ represents a hydrogen atom or a methyl radical;

and/or $R_3$ represents a 1-methyl-1H-pyrrol-2-yl; 1-methyl-1H-imidazol-2-yl; 1,3-thiazol-2-yl; 2-furyl; 3-furyl; 5-methyl-2-furyl; 4,5-dimethyl-2-furyl; 5-chloro-2-furyl; 2-thienyl; 3-thienyl; phenyl; pyridin-2-yl; pyridin-3-yl; pyridin-4-yl; pyrazin-2-yl; 6-methylpiridin-2-yl; 3-methyl-2-thienyl; 5-methyl-2-thienyl; pyrimidin-5-yl; 1H-imidazol-2-yl; 1H-imidazol-5-yl; or 4-methyl-1H-imidazol-5-yl radical.

Among these last preferred compounds particular preference is given to the compounds of formula (I) for which:

n is 1;

$R_1$ is in position 3 of the phenyl and represents a trifluoromethyl radical;

$R_2$ represents a hydrogen atom or a methyl radical;

$R_3$ represents a 1-methyl-1H-pyrrol-2-yl; 1-methyl-1H-imidazol-2-yl; 1,3-thiazol-2-yl; 2-furyl; 3-furyl; 5-methyl-2-furyl; 4,5-dimethyl-2-furyl; 5-chloro-2-furyl; 2-thienyl; 3-thienyl; phenyl; pyridin-2-yl; pyridin-3-yl; pyridin-4-yl; pyrazin-2-yl; 6-methylpiridin-2-yl; 3-methyl-2-thienyl; 5-methyl-2-thienyl; pyrimidin-5-yl; 1H-imidazol-2-yl; 1H-imidazol-5-yl; or 4-methyl-1H-imidazol-5-yl radical.

in the form of a base or an addition salt with an acid, and also in the form of a hydrate or solvate.

Among the compounds of formula (I) provided by the invention particular mention may be made of the following compounds:

[(1-methyl-1H-pyrrol-2-yl)methyl][[1-[(4-pyrazin-2-ylpiperazin-1-yl)acetyl]-4-[3-trifluoromethyl)phenyl] piperid-4-yl]methyl]amine;

N-methyl-1-(1-methyl-1H-imidazol-2-yl)-N-[[1-[(4pyrazin-2-ylpiperazin-1-yl)acetyl]-4-[3-(trifluoromethyl)phenyl]piperidin-4-yl]methyl]methanamine;

N-methyl-1-[1-[(4-pyrazin-2-ylpiperazin-1-yl)acetyl]-4-[3-(trifluoromethyl)phenyl]piperidin-4-yl]-N-(1,3-thiazol-2-ylmethyl)methanamine;

(2-furylmethyl)[[1-[(4-pyrazin-2-ylpiperazin-1-yl) acetyl]-4-[3-(trifluoromethyl)phenyl]piperidin-4-yl] methyl]amine;

(3-furylmethyl)[[1-[(4-pyrazin-2-ylpiperazin-1-yl) acetyl]-4-[3-(trifluoromethyl)phenyl]piperidin-4-yl] methyl]amine;

[(5-methyl-2-furyl)methyl][[1-[(4-pyrazin-2-ylpiperazin-1-yl)acetyl]-4-[3-(trifluoromethyl)phenyl]piperidin-4-yl]methyl]amine;

[(4,5-dimethyl-2-furyl)methyl]methyl[[1-[(4-pyrazin-2-ylpiperazin-1-yl)acetyl]-4-[3-(trifluoromethyl)phenyl] piperidin-4-yl]methyl]amine;

[(5-chloro-2-furyl)methyl]methyl[[1-[(4-pyrazin-2-ylpiperazin-1-yl)acetyl]-4-[3-(trifluoromethyl)phenyl]piperidin-4-yl]methyl]amine;

[[1-[(4-pyrazin-2-ylpiperazin-1-yl)acetyl]-4-[3-(trifluoromethyl)phenyl]piperidin-4-yl]methyl]-(2-thienylmethyl)amine;

[[1-[(4-pyrazin-2-ylpiperazin-1-yl)acetyl]-4-[3-(trifluoromethyl)phenyl]piperidin-4-yl]methyl]-(3-thienylmethyl)amine;

1-phenyl-N-[[1-[(4-pyrazin-2-ylpiperazin-1-yl)acetyl]-4-[3-(trifluoromethyl)phenyl]piperidin-4-yl]methyl]methanamine;

[[1-[(4-pyrazin-2-ylpiperazin-1-yl)acetyl]-4-[3-trifluoromethyl)phenyl]piperidin-4-yl]methyl]-(pyridin-2-ylmethyl)amine;

N-methyl-1-[1-[(4-pyrazin-2-ylpiperazin-1-yl)acetyl]-4-[3-(trifluoromethyl)phenyl]piperidin-4-yl]-N-(pyridin-2-ylmethyl)methanamine;

N-methyl-1-[1-[(4-pyrazin-2-ylpiperazin-1-yl)acetyl]-4-[3-(trifluoromethyl)phenyl]piperidin-4-yl]-N-(pyridin-3-ylmethyl)methanamine;

N-methyl-1-[1-[(4-pyrazin-2-ylpiperazin-1-yl)acetyl]-4-[3-(trifluoromethyl)phenyl]piperidin-4-yl]-N-(pyridin-4-ylmethyl)methanamine;

N-methyl-1-pyrazin-2-yl-N-[[1-[(4-pyrazin-2-ylpiperazin-1-yl)acetyl]-4-[3-(trifluoromethyl)phenyl]piperidin-4-yl]methyl]methanamine;

[(6-methylpiridin-2-yl)methyl][[1-[(4-pyrazin-2-ylpiperazin-1-yl)acetyl]-4-[3-(trifluoromethyl)phenyl]piperidin-4-yl]methyl]amine;

[(3-methyl-2-thienyl)methyl][[1-[(4-pyrazin-2-ylpiperazin-1-yl)acetyl]-4-[3-(trifluoromethyl)phenyl]piperidin-4-yl]methyl]amine;

N-methyl-1-(5-methyl-2-thienyl)-N-[[1-[(4-pyrazin-2-ylpiperazin-1-yl)acetyl]-4-[3-(trifluoromethyl)phenyl]piperidin-4-yl]methyl]methanamine;

N-methyl-1-[1-[(4-pyrazin-2-ylpiperazin-1-yl)acetyl]-4-[3-(trifluoromethyl)phenyl]piperidin-4-yl]-N-(pyrimidin-5-ylmethyl)methanamine;

(1H-imidazol-2-ylmethyl)methyl[[1-[(4-pyrazin-2-ylpiperazin-1-yl)acetyl]-4-[3-(trifluoromethyl)phenyl]piperidin-4-yl]methyl]amine;

(1H-imidazol-5-ylmethyl)methyl[[1-[(4-pyrazin-2-ylpiperazin-1-yl)acetyl]-4-[3-(trifluoromethyl)phenyl]piperidin-4-yl]methyl]amine;

N-methyl-1-(4-methyl-1H-imidazol-5-yl)-N-[[1-[(4-pyrazin-2-ylpiperazin-1-yl)acetyl]-4-[3-(trifluoromethyl)phenyl]piperidin-4-yl]methyl]methanamine;

in the form of base or an addition salt of an acid, and in the form of a hydrate or solvate.

In the text below, a protective group Pg is understood to be a group which makes it possible on the one hand for a reactive function such as an amine to be protected during a synthesis and on the other hand to regenerate the reactive function intact at the end of synthesis. Examples of protective groups and also of methods of protection and deprotection are given in "Protective Groups in Organic Synthesis", Green et al., 2nd Edition (John Wiley & Sons, Inc., New York).

A leaving group in the text below is understood as a group which is readily cleavable from a molecule by breaking of a heterolytic bond, with departure of an electron pair. This group may therefore easily be replaced by another group in the course of a substitution reaction, for example. Such leaving groups are, for example, halogens or an activated hydroxyl group such as a mesyl, tosyl, triflate, acetyl, etc. Examples of leaving groups and of references for their preparation are given in "Advances in Organic Chemistry", J. March, 3rd Edition, Wiley Interscience, pp. 310-316.

In accordance with the invention the compounds of formula (I) can be prepared by a process characterized in that:

a compound of formula:

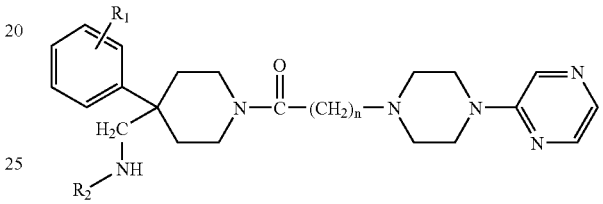

(II)

in which n, $R_1$ and $R_2$ are as defined for a compound of formula (I) is reacted with a compound of formula:

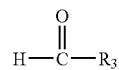

(III)

in which $R_3$ is as defined for a compound of formula (I) in the presence of an acid and in a solvent and then the iminium salt intermediately formed is reduced by means of a reducing agent.

Where appropriate, the compound of formula (I) is converted into one of its additional salts with an acid.

The reaction takes place in the presence of an acid such as acetic acid, in a solvent such as dichloromethane or tetrahydrofuran, at a temperature between the ambient temperature and the reflux temperature of the solvent, and forms in situ an intermediate imine which is reduced chemically using, for example, sodium cyanoborohydride or sodium triacetoxyborohydride or catalytically using hydrogen and a catalyst such as palladium on carbon or Raney® nickel.

The compounds of formula (I) thus obtained may finally be separated from the reaction mixture and purified in accordance with conventional methods, for example by crystallization or chromatography.

The compounds of formula (I) thus obtained are isolated in the form of the free base or in the form of a salt, in accordance with conventional techniques.

The compounds of formula (II) are prepared by deprotection reaction of a compound of formula:

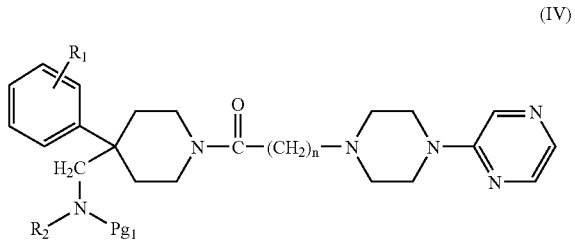

(IV)

in which n, $R_1$ and $R_2$ are as defined for a compound of formula (I) and $Pg_1$ represents a conventional N-protective group such as a tert-butoxycarbonyl group, a benzyloxycarbonyl group or a benzyl group. The deprotection reaction takes place in accordance with the methods cited above.

The compounds of formula (III) are available commercially or are described in the literature, or else may be prepared in accordance with methods which are described therein, such as in J. Org. Chem., 1961, 26, 2976; Chim. Ind. (Milan), 1968, 50, 264; J. Med. Chem., 1970, 13, 1208-1212; J. Heterocycl. Chem., 1990, 27(1), 1-12; Synth. Commun., 1995, 25(9), 1383-1390; Bioorg. Med. Chem. Lett., 2003, 13(3), 463-466.

The compounds of formula (IV) are prepared:

by reacting a compound of formula:

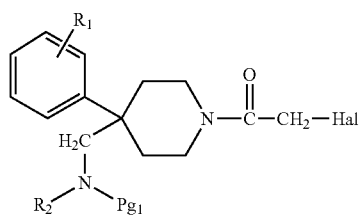

(Va)

in which $R_1$, $R_2$ and $Pg_1$ are as defined above and Hal represents a halogen atom, preferably chlorine or bromine, when the aim is to obtain a compound of formula (IV) in which n=1;

or by reacting a compound of formula:

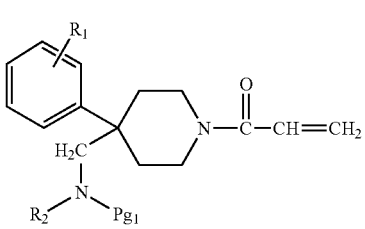

(Vb)

in which $R_1$, $R_2$ and $Pg_1$ are as defined above, when the aim is to obtain a compound of formula (IV) in which n=2;

with 1-(2-pyrazinyl)piperazine.

When a compound of formula (Va) or Vb) is reacted with 1-(2-pyrazinyl)piperazine, the reaction takes place in the presence of a base selected from organic bases such as triethylamine, N,N-diisopropylethylamine or N-methylmorpholine or from alkali metal carbonates or bicarbonates such as potassium carbonate, sodium carbonate or sodium bicarbonate and in the absence or presence of an alkali metal iodide such as potassium iodide or sodium iodide. The reaction takes place in a solvent such as acetonitrile, N,N-dimethylformamide, toluene or propan-2-ol and at a temperature between the ambient temperature and the reflux temperature of the solvent.

The compounds of formula (Va) are prepared by reacting a piperidine derivative of formula

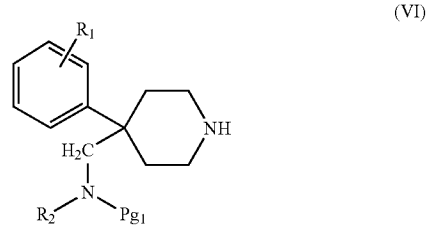

(VI)

in which $R_1$, $R_2$ and $Pg_1$ are as defined above, with a compound of formula

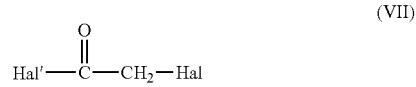

(VII)

in which Hal and Hal' represent each independently a halogen atom, preferably chlorine or bromine. The reaction is carried out in the presence of a base such as triethylamine, N,N-diisopropylethylamine or N-methylmorpholine in a solvent such as dichloromethane, tetrahydrofuran, dioxane or a mixture of these solvents and at a temperature between 0° C. and the ambient temperature.

The compounds of formula (Vb) are prepared by reacting the compound of formula (VI) with a compound of formula

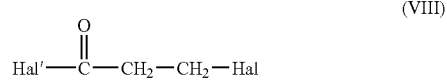

(VIII)

in which Hal and Hal' are as defined above under the operating conditions mentioned above.

The compounds of formula (VI) are prepared according to SCHEME 1 below in which $R_1$ and $R_2$ are as defined for a compound of formula (I) and $Pg_1$ and $Pg_2$ represent N-protective groups which are different from one another and are selected from the conventional N-protective groups well known to the skilled person.

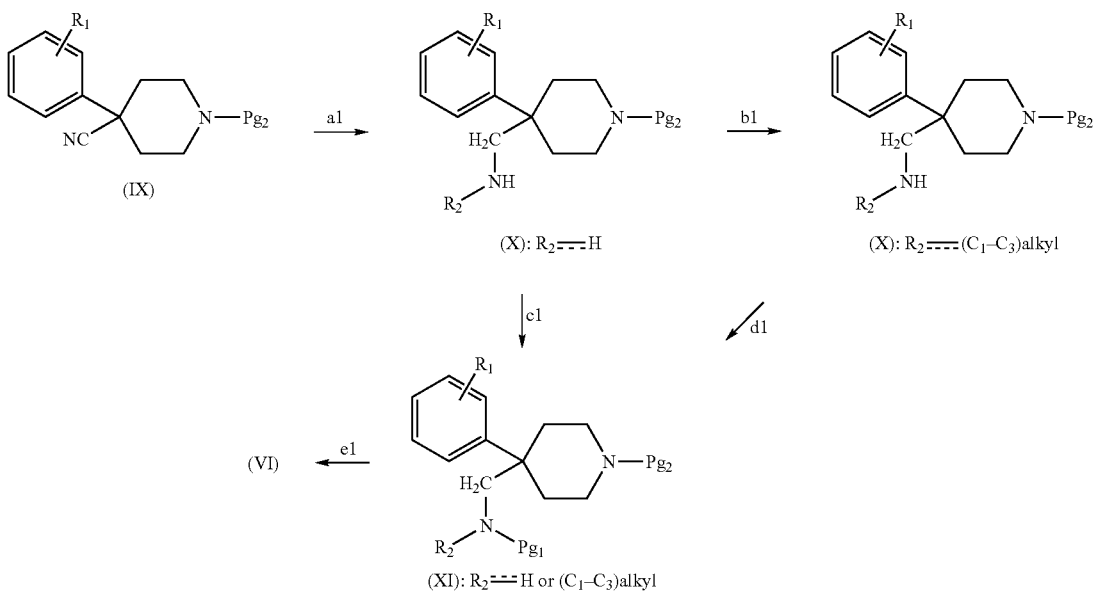

In step a1 the cyano group of a compound of formula (IX) is reduced to give a compound of formula (X) in which $R_2=H$. The reduction takes place, for example, by hydrogenation in the presence of a catalyst such as Raney® nickel or rhodium on alumina in the presence or absence of ammonia in a solvent such as methanol, N,N-dimethylformamide or tetrahydrofuran or a mixture of these solvents and at a temperature between the ambient temperature at 60° C.

A compound of formula (X) in which $R_2=(C_1-C_3)$alkyl is prepared, in step b1, by conventional alkylation reaction or by acylation reaction followed by reduction, starting from a compound of formula (X) in which $R_2=H$. Thus, for example, when the aim is to prepare a compound of formula (X) in which $R_2=-CH_3$, a compound of formula (X) in which $R_2=H$ is reacted with ethyl formate at a temperature between the ambient temperature and 60° C. and then the corresponding intermediate compound in which $R_2=-CHO$ is reduced by means of a reducing agent such as lithium aluminium hydride in a solvent such as diethyl ether or tetrahydrofuran and at a temperature between the ambient temperature and the reflux temperature of the solvent.

In step c1 or in step d1 the amine function of the compound of formula (X) is protected by introducing the N-protective group $Pg_1$, which is different from $Pg_2$, in accordance with conventional methods and then, in step e1, the N-protective group $Pg_2$ is removed in accordance with conventional methods to give the expected compound of formula (VI).

The compounds of formula (VII) or of formula (VIII) are available commercially, are known or are prepared by known methods.

The compounds of formula (IX) are prepared by known methods such as those described in Bioorg. Med. Chem. Lett., 1999, 9, 3273-3276 or in J. Med. Chem., 1999, 42 (23), 4778-4793.

1-(2-pyrazinyl)piperazine is a commercial product or is prepared by reacting piperazine with 2-chloropyrazine in the presence of a base such as an alkali metal carbonate, potassium carbonate for instance, in a solvent such as ethanol, propan-2-ol or n-butanol and at a temperature between the ambient temperature and the reflux temperature of the solvent.

EXAMPLES

The following examples describe the preparation of certain compounds in accordance with the invention. These examples are not limitative and merely illustrate the present invention. The numbers of the compounds exemplified refer to those given in Table I below, which illustrates the chemical structures and the physical properties of some compounds according to the invention.

In the preparations and in the examples the following abbreviations are used:

| | |
|---|---|
| ether: | diethyl ether |
| iso ether: | diisopropyl ether |
| DMSO: | dimethyl sulphoxide |
| DMF: | N,N-dimethylformamide |
| THF: | tetrahydrofuran |
| DCM: | dichloromethane |
| AcOEt: | ethyl acetate |
| DIPEA: | diisopropylethylamine |
| TFA: | trifluoroacetic acid |
| 2N hydrochloric ether: | 2N solution of hydrochloric acid in diethyl ether |
| m.p.: | melting point |
| AT: | ambient temperature |
| b.p.: | boiling temperature |
| HPLC: | high performance liquid chromatography |
| Silica H: | Silica gel 60 H sold by Merck (Darmstadt) |

Buffer solution pH=2: solution of 16.66 g of $KHSO_4$ and 32.32 g of $K_2SO_4$ in one litre of water.

The proton magnetic resonance ($^1H$ NMR) spectra are recorded at 200 MHz in DMSO-$d_6$, using the DMSO-$d_6$ peak as reference. The chemical shifts δ are expressed in parts per million (ppm). The signals observed are expressed as follows: s: singlet; bs: broad singlet; d: doublet; sd: split doublet; t:

triplet; st: split triplet; q; quadruplet; unres. comp.: unresolved complex; mt: multiplet.

The NMR spectra confirm the structures of the compounds.

The compounds according to the invention are analysed by LC/UV/MS (liquid chromatography/UV detection/mass spectrometry) coupling.

For the compounds a check is made that their mass spectra as obtained in the positive electrospray mode (ESI+) are compatible with the calculated molar mass.

The mass spectra of the compounds according to the invention generally have as their base peak the molecular ion MH+.

Preparations

1. Preparations of compounds of formula (VI).

Preparation 1.1 tert-Butyl [4-[3-(trifluoromethyl)phenyl]-4-piperidinyl]methylcarbamate (VI): $R_1$=3-$CF_3$; $R_2$=H; $Pg_1$=—COOC($CH_3$)$_3$.

A) 2-(2,2-Diethoxyethyl)-4,4-diethoxy-2-[3-(trifluoromethyl)phenyl]butanenitrile A mixture of 30 g of 3-(trifluoromethyl)-phenylacetonitrile and 14.4 g of sodium amide in 400 ml of toluene is left with stirring at AT for 5 minutes, 66 ml of bromoacetaldehyde diethyl acetal are added and then the mixture is heated at 60° C. for 3 hours. It is concentrated under vacuum, the residue is taken up with water and extracted with ether, the organic phase is dried over $Na_2SO_4$ and the solvent is evaporated under vacuum. The residue is chromatographed on silica gel H, eluting with a DCM/AcOEt (100/5; v/v) mixture. This gives 26 g of the expected product.

B) 4-Oxo-2-(2-oxoethyl)-2-[3-(trifluoromethyl)phenyl]butanenitrile

A mixture of 23.9 g of the compound obtained in the preceding step in 90 ml of formic acid is left with stirring at 50° C. for 1 hour. Water is added to the reaction mixture, which is then extracted with AcOEt, the organic phase is washed with water and with 10% $NaHCO_3$ solution and dried over $Na_2SO_4$ and the solvent is evaporated under vacuum. This gives 16 g of the expected product, which is used immediately in the following step.

C) 1-Benzyl-4-[3-(trifluoromethyl)phenyl]-4-piperidinecarbonitrile hydrochloride A mixture of 16 g of the compound obtained in the preceding step, 6.25 ml of benzylamine, 48.6 g of sodium triacetoxyborohydride and 5 drops of acetic acid in 150 ml of DCM is left with stirring at AT overnight. Subsequently 40 ml of MeOH are added dropwise and the mixture is then heated at 60° C. for 1 hour. The reaction mixture is concentrated under vacuum, the residue is extracted with AcOEt, the organic phase is washed with 10% $NaHCO_3$ solution and with water and dried over $Na_2SO_4$ and the solvent is evaporated under vacuum. The residue is taken up in a saturated solution of HCl gas in ether and the precipitate formed is isolated with suction. This gives 18 g of the expected product.

D) [1-Benzyl-4-[3-(trifluoromethyl)phenyl]-4-piperidinyl]methylamine

A mixture of 1.5 g of the compound obtained in step C of Preparation 1.4, 0.15 g of Raney® nickel and 5 ml of ammonia in 20 ml of MeOH is hydrogenated overnight at AT and under atmospheric pressure. The catalyst is filtered off and the filtrate is concentrated under vacuum. This gives 1.45 g of the expected product.

E) tert-Butyl [1-benzyl-4-[3-(trifluoromethyl)phenyl]-4-piperidinyl]methylcarbamate A mixture of 1.45 g of the compound obtained in the preceding step in 20 ml of AcOEt is heated to 40° C., 0.9 g of di-tert-butyl dicarbonate is added and then the mixture is heated at reflux for 30 minutes. After cooling to AT, water is added, extraction is carried out with AcOEt, the organic phase is dried over $Na_2SO_4$ and the solvent is evaporated under vacuum. This gives 1.86 g of the expected product.

F) tert-Butyl [4-[3-(trifluoromethyl)phenyl]-4-piperidinyl]methylcarbamate

A mixture of 1.8 g of the compound obtained in the preceding step and 0.18 g of 10% palladium on carbon in 20 ml of MeOH is hydrogenated at AT under atmospheric pressure overnight. The catalyst is filtered off and the filtrate is concentrated under vacuum. This gives 1.3 g of the expected product in the form of an oil.

Preparation 1.2 tert-Butylmethyl [[4-[3-(trifluoromethyl)phenyl]piperidin-4-yl]methyl]carbamate (VI): $R_1$=3-$CF_3$; $R_2$=—$CH_3$; $Pg_1$=—COOC($CH_3$)$_3$ A) N,N-Bis(2-chloroethyl)benzylamine Using an ice bath, a mixture of 150 g of N,N-bis(2-chloroethyl)amine hydrochloride and 100 ml of benzyl bromide in 1000 ml of DMF is cooled and then 120 ml of triethylamine are added dropwise and the mixture is left overnight with stirring at AT. The reaction mixture is concentrated under vacuum, the residue is taken up with water and extracted 3 times with ether, the organic phases are dried over $Na_2SO_4$ and the solvent is evaporated under vacuum. This gives 113 g of the expected product.

B) 1-Benzyl-4-[3-(trifluoromethyl)phenyl]-4-piperidinecarbonitrile hydrochloride A suspension of 23.24 g of 60% sodium hydride in oil in 100 ml of DMSO and 100 ml of THF is admixed dropwise under an inert atmosphere under AT with a solution of 50 g of 3-(trifluoromethyl)phenylacetonitrile in 150 ml of DMSO and the system is left for 15 minutes with stirring. Subsequently, over 1 hour, a solution of 62.43 g of the compound obtained in the preceding step in 150 ml of DMSO is added and the system is left overnight with stirring at AT. An ice/water mixture is added, the mixture is extracted with ether, the organic phase is dried over $Na_2SO_4$ and the solvent is evaporated under vacuum. The residue is taken up in 1000 ml of hot EtOH and left with stirring at AT for 48 hours and the crystalline product formed is filtered off with suction. This gives 50 g of the expected product.

C) [1-Benzyl-4-[3-(trifluoromethyl)phenyl]-4-piperidinyl]methylamine 30 g of the compound obtained in the preceding step is dissolved in 10% NaOH solution and extracted with ether, the organic phase is dried over Na₂SO₄ and the solvent is evaporated under vacuum. The product in the form of the free base is taken up in 500 ml of MeOH and 30 ml of 20% ammonia solution, 3 g of Raney® nickel are added and the mixture is hydrogenated overnight at AT and under atmospheric pressure. The catalyst is filtered off and the filtrate is concentrated under vacuum. The residue is taken up in water and extracted with AcOEt, the organic phase is dried over Na₂SO₄ and the solvent is evaporated under vacuum. This gives 27 g of the expected product.

D) [[1-Benzyl-4-[3-(trifluoromethyl)phenyl]-4-piperidinyl]methyl]formamide

A mixture of 27 g of the compound obtained in the preceding step and 300 ml of ethyl formate is left overnight with stirring at AT and then heated to 60° C. for 6 hours and left with stirring at AT for 48 hours. It is concentrated under vacuum, the residue is taken up in 10% HCl solution, the acidic aqueous phase is washed with ether, ice is added and the mixture is rendered alkaline by adding 10% NaOH solution and then extracted with ether, the organic phase is dried over Na₂SO₄ and the solvent is evaporated under vacuum. The residue is chromatographed on silica gel H, eluting with DCM and then with a DCM/MeOH (100/4; v/v) mixture. This gives 20 g of the expected product.

E) [[1-Benzyl-4-[3-(trifluoromethyl)phenyl]-4-piperidinyl]methyl]methylamine A suspension of 4 g of lithium aluminium hydride in 400 ml of ether is admixed at AT with 20 g of the compound obtained in the preceding step and then left for 16 hours with stirring at AT. Thereafter, in succession, 3 ml of water, 3 ml of 30% NaOH and 1 ml of water are added and the mixture is left with stirring. The inorganic salts are filtered off on Celite, the filtrate is decanted, the aqueous phase is dried over Na₂SO₄ and the solvent is evaporated under vacuum. This gives 18 g of the expected prodoct.

F) tert-Butyl [[1-benzyl-4-[3-(trifluoromethyl)phenyl]-4-piperidinyl]methyl]methylcarbamate A mixture of 18 g of the compound obtained in the preceding step and 9.6 g of di-tert-butyl dicarbonate in 300 ml of DCM is left with stirring at AT for 1 hour. Water is added to the reaction mixture and it is extracted with DCM, the organic phase is dried over Na₂SO₄ and the solvent is evaporated under vacuum. The residue is chromatographed on silica gel H, eluting with a DCM/MeOH (100/2; v/v) mixture. This gives 21 g of the expected product.

G) tert-Butylmethyl [4-[3-(trifluoromethyl)phenyl]-piperidin-4-yl]methyl]carbamate A mixture of 21 g of the compound obtained in the preceding step and 2 g of 10% palladium on carbon in 300 ml of MeOH is hydrogenated for 12 hours at AT under atmospheric pressure. The catalyst is filtered off and the filtrate is concentrated under vacuum. This gives 16 g of the expected product.

2. Preparations of compounds of formula (V).
Preparation 2.1 tert-Butyl [1-(2-chloroacetyl)-4-[3-(trifluoromethyl)phenyl]-4-piperidinyl]methylcarbamate (Va): $R_1$=3-$CF_3$; $R_2$=H; $Pg_1$=—COOC($CH_3$)$_3$; Hal=Cl.
Using an ice bath, a mixture of 4.95 g of the compound obtained in Preparation 1.1 and 6.8 ml of triethylamine in 50 ml of DCM is cooled, 1.65 ml of 2-chloroacetyl chloride are added dropwise and the mixture is left with stirring, allowing the temperature to return to AT. The mixture is concentrated under vacuum, the residue is taken up in saturated K₂CO₂ solution and extracted with AcOEt, the organic phase is washed with saturated K₂CO₃ solution, with a pH=2 buffer solution and with saturated NaCl solution and dried over Na₂SO₄ and the system is evaporated under vacuum. The residue is chromatographed on silica gel, eluting with a DCM/AcOEt (80/20; v/v) mixture. This gives 1.8 g of the expected product, which is used as it is.

Preparation 2.2 tert-Butyl [[1-(2-chloroacetyl)-4-[3-(trifluoromethyl)phenyl]-4-piperidinyl]methyl]methylcarbamate (Va): $R_1$=3-$CF_3$; $R_2$=—$CH_3$; $Pg_1$=—COOC($CH_3$)$_3$; Hal=Cl.
A solution of 14 g of the compound obtained in Preparation 1.2 and 5.5 ml of triethylamine in 300 ml of DCM is cooled to −40° C., 3.1 ml of 2-chloroacetyl chloride are added slowly and the mixture is left with stirring, allowing the temperature to return to AT. The mixture is concentrated under vacuum, the residue is taken up in water and extracted with AcOEt, the organic phase is washed with pH=2 buffer and with water and dried over Na₂SO₄ and the solvent is evaporated under vacuum. This gives 15.33 g of the expected product.

3. Preparations of compounds of formula (IV).
Preparation 3.1 tert-Butyl [1-[2-[4-(2-pyrazinyl)-1-piperazinyl]acetyl]-4-[3-(trifluoromethyl)phenyl]-4-piperidinyl]methylcarbamate (IV): $R_1$=3-$CF_3$; $R_2$=H; $Pg_1$=—COOC($CH_3$)$_3$; n=1.
A mixture of 2.8 g of the compound obtained in Preparation 2.1, 1.25 g of 1-(2-pyrazinyl)piperazine, 1.1 g of potassium iodide and 1.8 g of K₂CO₃ in 30 ml of acetonitrile is left with stirring at AT for 3 hours. Saturated K₂CO₃ solution is added, extraction is carried out with AcOEt, the organic phase is dried over Na₂SO₄ and the solvent is evaporated under vacuum. The residue is chromatographed on silica gel, eluting with a DCM/MeOH (97/3; v/v) mixture. This gives 1.75 g of the expected product.

Preparation 3.2 tert-Butylmethyl [[1-[2-[4-(2-pyrazinyl)-1-piperazinyl]acetyl]-4-[3-(trifluoromethyl)phenyl]-4-piperidinyl]methyl]carbamate (IV): $R_1$=3-$CF_3$; $R_2$=—$CH_3$; $Pg_1$=—COOC($CH_3$)$_3$; n=1.
A mixture of 10 g of the compound obtained in Preparation 2.2, 3.7 g of 1-(2-pyrazinyl)piperazine, 3.7 g of potassium iodide and 6.2 g of K₂CO₃ in 200 ml of acetonitrile is left with stirring at AT for 5 hours. The mixture is concentrated under vacuum, the residue is taken up in water and extracted with AcOEt, the organic phase is dried over Na₂SO₄ and the solvent is evaporated under vacuum. The residue is chromatographed on silica gel H, eluting with DCM and then with a DCM/MeOH (100/2; v/v) mixture. This gives 10.7 g of the expected product.

4. Preparations of compounds of formula (II).
Preparation 4.1

1-[4-(Aminomethyl)-4-[3-(trifluoromethyl)phenyl]-1-piperidinyl]-2-[4-(2-pyrazinyl)-1-piperazinyl]-1-ethanone (II): $R_1$=3-$CF_3$; $R_2$=H; n=1
A mixture of 1.7 g of the compound obtained in Preparation 3.1, 50 ml of a 2N HCl solution in ether and 30 ml of MeOH is left with stirring at AT for 4 hours. The mixture is concentrated under vacuum, the residue is taken up in water, the aqueous phase is washed with AcOEt, the aqueous phase is rendered alkaline by adding $K_2CO_3$, extraction is carried out with AcOEt, the organic phase is washed with saturated NaCl solution and dried over $Na_2SO_4$ and the solvent is evaporated under vacuum. The product crystallizes on evaporation in AcOEt and the crystals formed are filtered off with suction. This gives 1.05 g of the expected product, m.p.=152-153° C.

Mass spectrum: $MH^+$=463.3.

Preparation 4.2

1-[4-[(Methylamino)methyl]-4-[3-(trifluoromethyl)phenyl]-1-piperidinyl]-2-[4-(2-pyrazinyl)-1-piperazinyl]-1-ethanone (II): $R_1$=3-$CF_3$; $R_2$=—$CH_3$; n=1.

A solution of 8 g of the compound obtained in Preparation 3.2 and 100 ml of MeOH is admixed with 300 ml of 2N hydrochloric ether solution and left with stirring at AT overnight. The mixture is concentrated under vacuum, the residue is taken up in 10% NaOH solution and extracted with AcOEt, the organic phase is dried over $Na_2SO_4$ and the solvent is evaporated under vacuum. The residue is chromatographed on silica gel H, eluting with a DCM/MeOH (100/2; v/v) mixture and then with a DCM/MeOH/water (100/5/0.5; v/v/v) mixture. This gives 4.5 g of the expected product following recrystallization from iso ether, m.p.=137-139° C.

Mass spectrum $MH^+$=477.4.

$^1$H NMR: DMSO-$d_6$: δ (ppm): 1.10: s: 1H; 1.6-2.3: m: 7H; 2.4-3.8: m: 16H; 7.4-7.75: m: 4H; 7.8: d: 1H; 8.15: dd: 1H; 8.3: d: 1H.

Example 1

Compound 1

[(1-Methyl-1H-pyrrol-2-yl)methyl][[1-[(4-pyrazin-2-ylpiperazin-1-yl)acetyl]-4-[3-(trifluoromethyl)phenyl]piperidin-4-yl]methyl]amine (I): $R_1$=3-$CF_3$; $R_2$=H; $R_3$= 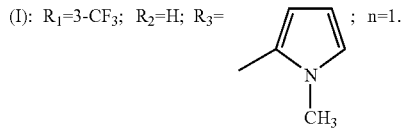 ; n=1.

A mixture of 1 g of a compound obtained in Preparation 4.1, 0.235 ml of 1-methyl-2-pyrrolecarboxaldehyde and 5 drops of acetic acid in 15 ml of THF is admixed in portions with 0.5 g of sodium triacetoxyborohydride and left with stirring at AT overnight. Then 20 ml of MeOH are added and the mixture is heated at 60° C. for 2 hours. It is concentrated under vacuum, the residue is taken up in 30% NaOH solution and extracted with DCM, the organic phase is dried over $Na_2SO_4$ and the solvent is evaporated under vacuum. The residue is chromatographed on silica gel, eluting with a DCM/MeOH (94/6; v/v) mixture. This gives 0.271 g of the expected product following recrystallization from an iso ether/DCM/ether mixture, m.p.=104-105° C.

Mass spectrum: $MH^+$=556.3.

Example 2

Compound 2

N-Methyl-1-(1-methyl-1H-imidazol-2-yl)-N-[[1-[(4-pyrazin-2-ylpiperazin-1-yl)acetyl]-4-[3-trifluoromethyl)phenyl]piperidin-4-yl]methyl]methanamine oxalate, dihydrate (I), $C_2H_2O_4$: $R_1$=3-$CF_3$; $R_2$=-$CH_3$; $R_3$= 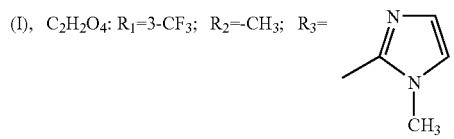 ; n=1.

A mixture of 0.5 g of a compound obtained in Preparation 4.2, 0.115 g of 1-methyl-1H-imidazol-2-carbaldehyde and 3 drops of acetic acid in 10 ml of THF is admixed in portions with 0.445 g of sodium triacetoxyborohydride and left with stirring at AT overnight. The mixture is concentrated under vacuum and the residue is taken up in 10 ml of MeOH and heated at 70° C. for 30 minutes. The mixture is concentrated under vacuum, the residue is taken up in 30% NaOH solution and extracted with DCM, the organic phase is dried over $Na_2SO_4$ and the solvent is evaporated under vacuum. The residue is chromatographed on silica gel H, eluting with a DCM/NaOH mixture from (100/1; v/v) to (100/5; v/v). The product obtained is taken up in ether, 0.082 g of oxalic acid is added, the mixture is left with stirring and the precipitate formed is filtered off with suction. This gives 0.23 g of the expected product, m.p.=80-100° C.

Mass spectrum: $MH^+$=571.6.

The table below illustrates the chemical structures and physical properties of some examples of compounds according to the invention. In this table:

in the "salt" column, "-" represents a compound in the form of the free base while "HCl" represents a compound in hydrochloride form and "$C_2H_2O_4$" represents a compound in oxalate form.

TABLE I

| Compounds | $R_1$ | $R_2$ | $R_3$ | n | Salt | m.p. ° C.; recrystallization solvent $MH^+$ |
|---|---|---|---|---|---|---|
| 1 | 3-$CF_3$ | H | ![pyrrole] | 1 | — | 104–105; iso ether/DCM/ether; 556.3 |

TABLE I-continued

Structure (I): A phenyl group with R1 substituent attached to a piperidine ring (4-position), which also bears a CH2-N(R2)(CH2-R3) group. The piperidine N is acylated with -C(O)-(CH2)n-N(piperazine)-pyrazinyl.

| Compounds | R₁ | R₂ | R₃ | n | Salt | m.p. °C; recrystallization solvent; MH⁺ |
|---|---|---|---|---|---|---|
| 2 | 3-CF₃ | —CH₃ | 1-methyl-2-imidazolyl (N-CH₃) | 1 | C₂H₂O₄ | 80–100; ether; 571.6 |
| 3 (a) | 3-CF₃ | —CH₃ | 2-methylthiazolyl | 1 | 3HCl | —; ether; 574.3 |
| 4 (b) | 3-CF₃ | H | 2-methylfuryl | 1 | — | 133–134; MeOH/ether; 543.3 |
| 5 (b) | 3-CF₃ | H | 3-methylfuryl | 1 | — | 147; ether/DCM; 543.3 |
| 6 (b) | 3-CF₃ | H | 2,5-dimethylfuryl | 1 | — | 110–113; iso ether/DCM; 557.5 |
| 7 (a) | 3-CF₃ | —CH₃ | 2,4,5-trimethylfuryl | 1 | 3HCl | —; ether; 585.4 |
| 8 (a) | 3-CF₃ | —CH₃ | 5-chloro-2-methylfuryl | 1 | — | 100–102; iso ether/DCM; 591.4 |
| 9 (b) | 3-CF₃ | H | 2-methylthienyl | 1 | — | 140–141; DCM/iso ether; 559.3 |
| 10 (b) | 3-CF₃ | H | 3-methylthienyl | 1 | — | 125–126; iso ether/DCM; 559.3 |
| 11 (b) | 3-CF₃ | H | phenyl | 1 | — | 120; —; 553.5 |
| 12 (b) | 3-CF₃ | H | 2-pyridyl | 1 | — | 104–105; iso ether; 554.4 |
| 13 (a) | 3-CF₃ | —CH₃ | 2-pyridyl | 1 | — | 110–111; iso ether/DCM; 568.5 |
| 14 (a) | 3-CF₃ | —CH₃ | 3-pyridyl | 1 | 4HCl | —; ether; 568.4 |
| 15 (a) | 3-CF₃ | —CH₃ | 4-pyridyl | 1 | 4HCl | —; ether; 568.4 |
| 16 (a) | 3-CF₃ | —CH₃ | 2-methylpyrazinyl | 1 | 4HCl | —; ether; 569.4 |
| 17 (b) | 3-CF₃ | H | 2,6-dimethylpyridyl | 1 | — | 118–123; DCM/iso ether; 568.2 |
| 18 (b) | 3-CF₃ | H | 2,3-dimethylthienyl | 1 | 3HCl | —; ether; 573.2 |
| 19 (a) | 3-CF₃ | —CH₃ | 2,5-dimethylthienyl | 1 | HCl | —; ether; 587.2 |
| 20 (a) | 3-CF₃ | —CH₃ | 5-methylpyrimidinyl | 1 | — | 161; DCM/iso ether; 569.2 |
| 21 (a) | 3-CF₃ | —CH₃ | 2-methylimidazolyl (NH) | 1 | — | 101–108; iso ether/DCM; 557.2 |
| 22 (a) | 3-CF₃ | —CH₃ | 4-methylimidazolyl (NH) | 1 | 4HCl | —; ether; 557.2 |

TABLE I-continued

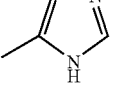

| Com- pounds | $R_1$ | $R_2$ | $R_3$ | n | Salt | m.p. °C.; recrystal- lization solvent $MH^+$ |
|---|---|---|---|---|---|---|
| 23 (a) | 3-$CF_3$ | —$CH_3$ | H₃C—[imidazole] | 1 | — | 150–152 iso ether/ DCM; 571.2 |

(a) Compound prepared by the procedure described in Example 2, from the compound of Preparation 4.2 and the corresponding compound of formula (III).
(b) Compound prepared by the procedure described in Example 1, from the compound of Preparation 4.1 and the corresponding compound of formula (III).

The compounds according to the invention were subjected to biochemical studies.

Cell Culture:

The SH-SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM), anti-PPLO (5 ml) (antimycoplasma agent: Tylocine® prepared in a normal saline solution, 6 000 µg/ml), gentamycin (0.1 mg/ml) and glutamine (4 mM) in collagen-coated culture flasks (Becton Dickinson, France).

The stock strain SK-N-BE (human neuroblastoma) and the clone Bep 75 expressing the human $p75^{NTR}$ receptor (SK-N-BE Bep 75) are conventionally cultured in a DMEM culture medium containing FCS (5%), sodium pyruvate (1 mM), anti-PPLO (5 ml), gentamycin (0.1 mg/ml) and glutamine (4 mM).

Study of the Binding of $^{125}$I-NGF to the $p75^{NTR}$ Receptor

The study of the binding of $^{125}$I-NGF (neuronal growth factor radiolabelled with iodine-125) is carried out on a cellular suspension of the two strains SH-SY-5Y and SK-N-BE Bep 75 in accordance with the method described by Weskamp (Neuron, 1991, 6, 649-663). Nonspecific binding is determined by measuring the total binding after one hour of preincubation with the cells at 37° C. in the presence of nonradiolabelled NGF (1 µM). The specific binding is calculated by the difference between the measurement of total binding and the measurement of nonspecific binding. The competition experiments are carried out using a $^{125}$I-NGF concentration of 0.3 nM. The concentrations inhibiting by 50% ($IC_{50}$) the binding of $^{125}$I-NGF to the $p75^{NTR}$ receptor of the compound according to the invention are low and vary from $10^{-6}$ to $10^{-11}$ M.

Measurement of Apoptosis:

The cells (human neuroblastoma strains SH-SY-5Y and SK-N-BE Bep 75) are established in Petri dishes 35 mm in diameter (Biocoat collagen I) ($10^5$ cells/well) in a DMEM culture medium containing 5% FCS for 24 h. The culture medium is then removed, the cells are rinsed with PBS (Dulbecco's phosphate buffered saline) and either fresh medium containing 5% FCS or medium containing NGF at the concentration of 10 ng/ml is added in the presence or absence of the compounds according to the invention. The levels of apoptosis are measured 48 hours after the treatments in the case of the strain SH-SY-5Y and 24 hours later in the case of the strain SK-N-BE Bep 75 by quantifying the cytoplasmic histones associated with the DNA fragments (cell death detection ELISA, Boehringer Mannheim, Germany). The levels of apoptosis are expressed as quantity of oligonucleosomes/$10^5$ cells±SD. Each value corresponds to the mean of 9 experimental points distributed over 3 independent experiments. The compounds of formula (I) exhibit NGF-induced apoptosis inhibitory activity with $IC_{50}$ values varying from $10^{-6}$ to $10^{-11}$ M.

Thus the binding of the compounds according to the invention to the $p75^{NTR}$ receptor results, on the one hand, at the biochemical level, in the inhibition of the dimerization of the receptor induced by neurotrophins, and, on the other hand, at the cellular level, in the inhibition of the proapoptotic effect mediated by the $p75^{NTR}$ receptor.

The compounds according to the invention can therefore be used for the preparation of medicaments, in particular of medicaments intended for the prevention or treatment of any pathology where the $p75^{NTR}$ receptor is involved.

Thus, in another of its aspects, the invention provides medicaments comprising a compound of formula (I), or an addition salt thereof with a pharmaceutically acceptable acid, or alternatively a solvate or a hydrate of the compound of formula (I).

Thus the compounds according to the invention may be used, in humans or in animals, in the treatment or prevention of various $p75^{NTR}$-dependent conditions such as central and peripheral neurodegenerative diseases such as senile dementia, epilepsy, Alzheimer's disease, Parkinson's disease, Huntington's chorea, Down's syndrome, prion diseases, amnesia, schizophrenia; amyotrophic lateral sclerosis, multiple sclerosis; cardiovascular conditions such as post-ischaemic cardiac damage, cardiomyopathies, myocardial infarction, cardiac insufficiency, cardiac ischaemia, cerebral infarction; peripheral neuropathies (of diabetic, traumatic or iatrogenic origin); damage to the optic nerve and to the retina; spinal cord trauma and cranial trauma; atherosclerosis; stenoses; cicatrization; alopecia.

The compounds according to the invention may also be used in the treatment of cancers such as that of the lung, of the thyroid, of the pancreas, of the prostate, of the small intestine and of the colon, of the breast, in the treatment of tumours, of metastases and of leukaemias.

The compounds according to the invention may also be used in the treatment of chronic neuropathic and inflammatory pain and in the treatment of autoimmune diseases such as rheumatoid arthritis.

The compounds according to the invention may also be used in the treatment of bone fractures and in the treatment or prevention of bone diseases such as osteoporosis.

In another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and at least one pharmaceutically acceptable excipient.

The said excipients are selected, according to the pharmaceutical form and the desired mode of administration, from the customary excipients which are known to the person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, solvate or hydrate where appropriate, may be administered in unit form for administration, as a mixture with conventional pharmaceutical excipients, to animals and to human beings for the prophylaxis or treatment of the above disorders or diseases.

The appropriate unit forms for administration comprise the forms for oral administration such as tablets, soft or hard gelatin capsules, powders, granules and oral solutions or suspensions, forms for sublingual, buccal, intratracheal, intraocular or intranasal administration, forms for administration by inhalation, forms for topical, transdermal, subcutaneous, intramuscular or intravenous administration, forms for rectal administration and implants. For topical application, the compounds according to the invention may be used in creams, gels, ointments or lotions.

By way of example, a unit form for administration of a compound according to the invention in tablet form may comprise the following components:

| | |
|---|---|
| Compound of the invention | 50.0 mg |
| Mannitol | 223.75 mg |
| Croscarmellose sodium | 6.0 mg |
| Cornstarch | 15.0 mg |
| Hydroxypropylmethylcellulose | 2.25 mg |
| Magnesium stearate | 3.0 mg |

For oral administration, the dose of active principle administered per day may be up to 0.01 to 100 mg/kg, in single or divided doses, preferably 0.02 to 50 mg/kg.

There may be particular cases in which higher or lower dosages are appropriate; such dosages are not outside the scope of the invention. According to the customary practice, the dosage appropriate for each patient is determined by the doctor according to the mode of administration, the weight and the response of the said patient.

The present invention, in another of its aspects, also relates to a method of treating the pathologies indicated above which comprises the administration, to a patient, of an effective dose of a compound according to the invention, or one of its pharmaceutically acceptable salts or its hydrates or solvates.

We claim:

1. A compound of formula (I):

(I)

wherein:

n is 1 or 2;

$R_1$ is trifluoromethyl;

$R_2$ is hydrogen or $(C_1-C_3)$alkyl;

$R_3$ is an aromatic group selected from:

wherein the aromatic group is unsubstituted or mono- or disubstituted by a substituent selected independently from halogen, $(C_1-C_3)$alkyl or $(C_1-C_3)$alkoxy; and $R_4$ is hydrogen or $(C_1-C_3)$alkyl;

or an addition salt with an acid thereof.

2. The compound according to claim 1, wherein:

n is 1;

or an addition salt with an acid thereof.

3. The compound according to claim 1, wherein:

$R_1$ is in position 3 of the phenyl and is trifluoromethyl;

or an addition salt with an acid thereof.

4. The compound according to claim 1, wherein:

$R_2$ is hydrogen or methyl;

or an addition salt with an acid thereof.

5. The compound according to claim 1, wherein:

$R_3$ is 1-methyl-1H-pyrrol-2-yl; 1-methyl-1H-imidazol-2-yl; 1,3-thiazol-2-yl; 2-furyl; 3-furyl; 5-methyl-2-furyl; 4,5-dimethyl-2-furyl; 5-chloro-2-furyl; 2-thienyl; 3-thienyl; phenyl; pyridin-2-yl; pyridin-3-yl; pyridin-4-yl; pyrazin-2-yl; 6-methylpyridin-2-yl; 3-methyl-2-thienyl; 5-methyl-2-thienyl; pyrimidin-5-yl; 1H-imidazol-2-yl; 1H-imidazol-5-yl; or 4-methyl-1H-imidazol-5-yl; or an addition salt with an acid thereof.

6. The compound according to claim 1, wherein:

n is 1;

$R_1$ is in position 3 of the phenyl and is trifluoromethyl;

$R_2$ is hydrogen or methyl; and $R_3$ is 1-methyl-1H-pyrrol-2-yl; 1-methyl-1H-imidazol-2-yl; 1,3-thiazol-2-yl; 2-furyl; 3 -furyl; 5-methyl-2-furyl; 4,5-dimethyl-2-furyl; 5-chloro-2-furyl; 2-thienyl; 3-thienyl; phenyl; pyridin-2-yl; pyridin-3-yl; pyridin-4-yl; pyrazin-2-yl; 6-methylpyridin-2-yl; 3-methyl-2-thienyl; 5-methyl-2-thienyl; pyrimidin-5-yl; 1H-imidazol-2-yl; 1H-imidazol-5-yl; or 4-methyl-1H-imidazol-5-yl; or an addition salt with an acid thereof.

7. A process for preparing the compound according to claim 1, comprising:

reacting a compound of formula (II)

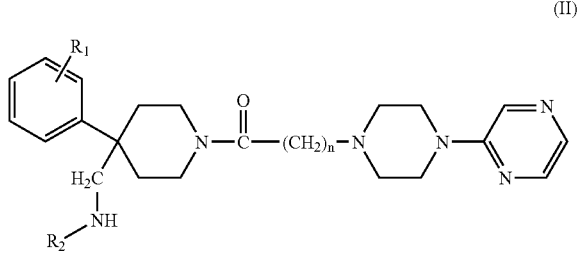

wherein n, $R_1$ and $R_2$ are as defined in claim 1, with a compound of formula (III)

wherein $R_3$ is as defined in claim 1, in the presence of an acid and in a solvent to form an iminium salt, and reducing the iminium salt by a reducing agent.

8. A pharmaceutical composition comprising the compound according to claim 1, or an addition salt with an acid thereof, and at least one pharmaceutically acceptable excipient.

9. A pharmaceutical composition comprising the compound according to claim 2, or an addition salt with an acid thereof, and at least one pharmaceutically acceptable excipient.

10. A pharmaceutical composition comprising the compound according to claim 3, or an addition salt with an acid thereof, and at least one pharmaceutically acceptable excipient.

11. A pharmaceutical composition comprising the compound according to claim 4, or an addition salt with an acid thereof, and at least one pharmaceutically acceptable excipient.

12. A pharmaceutical composition comprising the compound according to claim 5, or an addition salt with an acid thereof, and at least one pharmaceutically acceptable excipient.

13. A pharmaceutical composition comprising the compound according to claim 6, or an addition salt with an acid thereof, and at least one pharmaceutically acceptable excipient.

14. A method for treating chronic neuropathic or inflammatory pain in a patient in need thereof, comprising administering to the patient a pharmaceutically effective amount of the compound according to claim 1, or an addition salt with an acid thereof.

* * * * *

UNITED STATES PATENT AND TRADEMARK OFFICE
CERTIFICATE OF CORRECTION

PATENT NO. : 7,652,011 B2  Page 1 of 1
APPLICATION NO. : 11/420505
DATED : January 26, 2010
INVENTOR(S) : Bosch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

Twenty-third Day of November, 2010

David J. Kappos
*Director of the United States Patent and Trademark Office*